United States Patent
Benita et al.

[11] Patent Number: 6,007,826
[45] Date of Patent: Dec. 28, 1999

[54] OIL-IN-WATER EMULSIONS OF POSITIVELY CHARGED PARTICLES

[75] Inventors: Simon Benita, Mevasseret Sion; Efrat Elbaz, Jerusalem, both of Israel

[73] Assignee: Yisum Research Development Company of the Hebrew University of Jerusalem, Jerusalem, Israel

[21] Appl. No.: 08/730,577

[22] Filed: Oct. 15, 1996

Related U.S. Application Data

[63] Continuation of application No. 08/302,761, filed as application No. PCT/US93/02303, Mar. 15, 1993.

[30] Foreign Application Priority Data

Mar. 16, 1992 [IL] Israel .................................. 101241

[51] Int. Cl.⁶ ......................................... A61K 9/10
[52] U.S. Cl. ..................... 424/401; 424/450; 514/941; 514/943; 516/56
[58] Field of Search ............................. 252/312; 424/450, 424/401; 514/941, 943; 516/56

[56] References Cited

U.S. PATENT DOCUMENTS

| | | | |
|---|---|---|---|
| 3,658,718 | 4/1972 | Clumpner | 252/357 |
| 4,320,121 | 3/1982 | Sears | 252/316 |
| 4,647,586 | 3/1987 | Mizushima et al. | 514/943 |
| 4,670,185 | 6/1987 | Fujiwara et al. | 252/312 X |
| 4,919,923 | 4/1990 | Hoeffkes et al. | 514/938 X |
| 5,019,369 | 5/1991 | Presant et al. | 424/450 |
| 5,165,994 | 11/1992 | Kaler et al. | 424/450 X |
| 5,182,267 | 1/1993 | Ogawa et al. | 514/35 |
| 5,188,837 | 2/1993 | Domb | 424/450 |
| 5,283,185 | 2/1994 | Epand et al. | 435/172.3 |
| 5,466,458 | 11/1995 | Martin et al. | 424/405 |
| 5,496,818 | 3/1996 | Schaupp et al. | 514/225.8 |
| 5,534,502 | 7/1996 | Seki et al. | 514/943 |
| 5,576,016 | 11/1996 | Amselem et al. | 424/450 |

FOREIGN PATENT DOCUMENTS

| | | |
|---|---|---|
| 394847 | 10/1910 | European Pat. Off. . |
| 171084 | 2/1986 | European Pat. Off. . |
| 0348942 | 1/1990 | European Pat. Off. . |
| 0349150 | 1/1990 | European Pat. Off. . |
| 355604 | 2/1990 | European Pat. Off. . |
| 372331 | 6/1990 | European Pat. Off. . |
| 0391369 | 10/1990 | European Pat. Off. . |
| 456106 | 11/1991 | European Pat. Off. . |
| 490053 | 6/1992 | European Pat. Off. . |
| 521799 | 1/1993 | European Pat. Off. . |
| 2455458 | 11/1980 | France . |
| 1-113315 | 5/1989 | Japan . |
| 9010429 | 9/1990 | WIPO . |

OTHER PUBLICATIONS

PTO 97–5393, Translation Japan Kokai 1–113315, USPTO, Wash., DC, Oct. 1997.

Chem. Abstr., vol. 111, No. 20, 13 Nov. 1989 (Columbus OH, USA) P. 429, Col. 1, Abstr. 180758v, LEDERLE (Japan) LTD., Jpn Kokai Tokyo Koho Jp 01 113,315 (Japanese) Nov. 1989.

Milton J. Rosen, Surfactants and Interfacial Phenomena, (Wiley–Interscience publications, 1978, NY, NY) pp. 224–225, 1978, month unknown.

Journal of Colloid and Interface Science, vol. 33, pp. 468–470, Jul. 1970.

Hawley's Condensed Chemical Dictionary, Eleventh Edition, (Van Nostrand reinhold Co., Inc., NY, NY), 1987.

*Primary Examiner*—Richard D. Lovering
*Assistant Examiner*—Daniel S. Metzmaier
*Attorney, Agent, or Firm*—Helfgott & Karas, P.C.

[57] ABSTRACT

An oil-in-water emulsion useful as a delivery vehicle of hydrophobic ingredients such as pharmaceutical drugs and cosmetic active agent; wherein the emulsion particles have a net positive charge (i.e. a positive zeta potential).

18 Claims, 11 Drawing Sheets

OIL-IN-WATER EMULSIONS OF POSITIVELY CHARGED PARTICLES

This application is a continuation of application Ser. No. 08/302,761, filed Nov. 2, 1994, now abandoned and which was filed under 35 U.S.C. 371 and based on PCT/US93/02303, filed Mar. 15, 1993.

FIELD OF THE INVENTION

The present invention concerns oil-in-water type emulsions useful as a delivery vehicle of hydrophobic active ingredients such as pharmaceutical drugs or cosmetically active agents. The emulsions of the present invention are characterized in that their colloid particles are positively charged.

BACKGROUND OF THE INVENTION AND PRIOR ART

In recent years, oil-in-water type emulsions, in particularly such in which the droplets are of a submicron size (hereinafter "submicron emulsions") gained increasing importance as vehicles for delivery of hydrophobic drugs. Formulations of submicron emulsions reported in the literature to date were usually based on a combination of lecithins which are mixtures of phospholipids of various compositions obtained from natural sources, non-ionic or ionic surfactants and of oil such as vegetable oil. Lecithins generally comprise phosphatidylcholine as the major component, which is a zwitterion that is neutral over a wide pH range, and negatively charged phospholipids such as phosphatidylethanolamine, phosphatidylserine and phosphatidic acid. As a consequence of their composition, the colloid particles in all emulsions available to date were negatively charged.

In order to increase stability of emulsions it was generally accepted that the charge of the colloid particles, or the so called "zeta potential", should be made as negative as possible, e.g. by the addition of various non-ionic or also negatively charged surfactants. However, negatively charged particles have a tendency of absorption of cations such as sodium and calcium ions which are present in all physiological fluids. Such absorption decreases the net surface charge of the particles and may eventually cause the breakdown of the droplets and the coalesence of small droplets to form larger ones. For the long term stability of such emulsions it was always necessary to prepare them with deionized water. A further problem of such emulsions resides in that the surface of biological membranes is generally negatively charged and there is thus an electrostatic repulsion between such membranes and the negatively charged colloid particles of the emulsion. This is at times a serious drawback for various applications.

Thus, against the very high potential of emulsions, and in particularly submicron emulsions, as drug delivery of vehicles, there are the above noted drawbacks.

European Patent Application 372331 discloses oil-in-water type emulsions, for parenteral administration which contain phospholipids as emulsifiers and being characterized in that they comprise physiologically acceptable concentrations of non-toxic divalent or trivalent metal cations so that the zeta potential is in the range of (+)8–20 millivolts. As disclosed in this patent application, the emulsions are not destabilized by the addition of electrolytes and are useful for making a total nutrient, electrolyte-containing parenteral feeding systems. These nutritional emulsions, however, are not suitable as drug delivery systems of hydrophobic drugs since they are sensitive to the incorporation of drugs to their inner oil phase which causes a phase separation. Furthermore, upon introduction of the emulsions into a physiological fluid, introduction of the emulsions into a physiological fluid, e.g. blood, the concentration of the divalent and the trivalent cations immediately decreases as a result dilution and of the very strong buffering potential of physiological fluids and accordingly the particles are likely to break down. Such breakdown may be of little consequence where the emulsion is used for the purpose of nutrition but it renders such emulsions unsuitable for use as drug delivery vehicles.

It is an object of the present invention to provide novel oil-in-water type emulsions useful as drug delivery vehicles which overcome some of the above noted drawbacks of the prior art.

It is a further object of the present invention to provide novel oil-in-water type emulsions wherein the colloid particles are positively charged as a result of the combined properties of the surface active substances, i.e. without the need to add cations.

GENERAL DESCRIPTION OP THE INVENTION

The present invention provides a novel oil-in-water type emulsion useful as a delivery vehicle of pharmaceutically or cosmetically active hydrophobic substances for various pharmaceutical or cosmetic applications. The pharmaceutically or cosmetically active substances in the emulsions will be referred to herein at times by the term "active ingredient". Where the active ingredient is pharmaceutically active it will at times be referred to herein as "drug".

An oil-in-water type emulsion generally comprises tiny colloid particles suspended in an aqueous solution.

Each colloid particle has an oily core comprising the oily carrier of the emulsion and an external layer comprising the emulsifiers and the surface active substances. In the description below, the following terms will at times be used: "aqueous phase" to denote the aqueous solution of the emulsion; "oily phase" to denote the oily cores of the particles; and "interfacial film" to denote the layer surrounding the cores of the particles.

Depending on the nature of the film substances, the external surface of the colloid particles may be charged. This charge is known in the art as the "zeta potential".

The present invention provides an oil-in-water type emulsion which comprises colloid particles having an oily core surrounded by an interfacial film, the film comprising surface active agents, lipids or both, said emulsions being characterized in that at least part of the surface active agents or lipids in the interfacial film have positively charged polar groups and further in that the colloid particles have a positive zeta potential.

In addition to surface active agents and/or lipids with positively charged polar groups (hereinafter: "cationic surfactants") the interfacial film may also comprise non-ionic surfactants or lipids and also surface active agents having a negatively charged polar group (hereinafter: "anionic surfactants"). In order to have a positive zeta potential the total charge of the cationic surfactants should be in excess to the total charge of the anionic surfactants.

Example of cationic lipids are, $C_{10}$–$C_{24}$-alkylamines and $C_{12}$–$C_{24}$-alkanolamines, $C_{12}$–$C_{18}$-alkylamines and $C_{12}$–$C_{18}$-alkanolamines being preferred. Specific examples of cationic lipids are stearylamine, oleylamine and cholesteryl betainate and various cationic cholesterol esters and derivatives.

Examples of anionic lipids particularly in emulsions intended for pharmaceutical use are phospholipids. Examples of phospholipids which may be used in the emulsions of the invention are lecithins; Epikuron 120™ (Lucas Meyer, Germany) which is a mixture of about 70% phosphatidylcholine and 12% phosphatidylethanolamine and about 15% other phospholipids; Ovothin 160™ or Ovothin 200™ (Lucas Meyer, phosphatidylcholine, 18% phosphatidylethanolamine and 12% other phospholipids; a purified phospholipid mixture, e.g. such which is obtained from egg yolk; Lipoid E-80™ (Lipoid AG, Ludwigshafen, Germany) which is a phospholipid mixture comprising about 80% phosphatidylcholine, 8% phosphatidylethanolamine, 3.6% non-polar lipids and about 2% sphingomyeline.

Examples of anionic surfactants which may be included particularly in emulsions intended for various cosmetic uses such as in hair shampoo and other body-care preparations are sodium lauryl sulphate and alkylpolyoxyethelene sulphate and sulfonate.

Examples of non-ionic surfactants which may be included in the emulsion of the invention are poloxamers such as Pluronic F-68LF™, Pluronic L-62LF™ and Pluronic L62D™ (BASF Wyandotte Corp., Parsippany, N.J., USA), tyloxapol, polysorbate such as polysorbate 80, polyoxyethylene fatty acid esters such as EMULPHOR™ (GAF Corp., Wayne, N.J., USA).

The oily phase of the emulsion may comprise one or more members selected from the group consisting of vegetable oil, mineral oil, medium chain triglyceride (MCT) oil (i.e. a triglyceride oil in which the carbohydrate chain has about 8–12 carbon atoms), oily fatty acid, isopropyl myristate, oily fatty alcohols, esters of sorbitol and fatty acids, oily sucrose esters, and in general any oily substance which is physiologically tolerated.

The major component of the oily phase will generally be either vegetable oil and/or MCT. Fatty acids or fatty alcohols may be included in cases where the hydrophobic substance to be carried by the emulsion is not sufficiently soluble in the oily phase such as in the case of the drug Diazepam.

MCT oil has many advantages over vegetable oil, amongst which are the following: lower disceptability to oxidation; having a specific density of about 0.94–0.95 which oxidation; having a specific density of about 0.94–0.95 which is higher than that of vegetable oil and which is closer to that of water, thus facilitating the obtaining of a stable emulsion; being less hydrophobic than vegetable oil and therefore allowing achieving of higher concentrations of substances dissolved therein; having a low viscosity which again allows increase in concentration of the oily phase in the emulsion while still having the viscosity within a reasonable range.

On the other hand, vegetable oil has the advantage over MCT oil in its lower price. Thus, although the use of MCT as the major component of the oily phase is generally preferred, it may at times be practical to substitute some of it with vegetable oil.

Examples of MCT oil which may be used in emulsions of the present invention are TCM™ (Societe des Oleagineux, France), Miglyol 812™ (Dynamit Novel, Sweden). Examples of vegetable oil which may be used in emulsions of the present invention are soybean oil, cottonseed oil, olive oil and sesame oil.

Examples of oily fatty acids which may be used in emulsions of the invention are oleic acid, linoleic acid, lauric acid and others. Examples of fatty alcohols which may be used are oleyl alcohol, cetyl alcohol and others. Examples of esters of sorbitol and fatty acids are sorbitan monooleate and sorbiton mono-palmitate. Examples of oily sucrose esters are sucrose mono-, di-or tri-palmitate.

As is known, the emulsion may also comprise various additives such as osmotic pressure regulators, e.g. sucrose or glycerine; anti-oxidants, e.g. α-tocopherol and ascorbic acid; or preservatives, e.g. methyl-, ethyl-, and butyl paraben.

Emulsions in accordance with the present invention may be formulated with various hydrophobic active ingredients for a large number of pharmaceutical and cosmetic applications. The emulsions may be formulated for topical, parenteral, ocular and oral administration of said active ingredients. Where an emulsion of the present invention is to be used for parenteral administration, it must be sterile, which sterility is preferably achieved by autoclaving, although other forms of sterilization such as filtration may also in principle be used. The constituents of emulsions intended for parenteral administration have to be of injection grade and medically approved for such administration.

Where the emulsion is formulated for topical or ocular application, particularly for topical cosmetic application, it is suitably supplemented with gel forming polymers, which are known per se, in order to increase the viscosity of the formulation.

In the following, concentrations of the ingredients of the emulsion will be given as "%", meaning weight of ingredient in hundred weight units of total composition ("w/w").

An injectable emulsion should not be too viscous. As a rule, the viscosity of an emulsion increases with an increase in the proportion of the non-aqueous phase, which comprises the oily carrier, the surface active agents or lipids and the hydrophobic active ingredient. It is accordingly preferred in accordance with the present invention that the proportion of the non-aqueous phase in injectable emulsions should not exceed about 30%. It is even more preferred in accordance with the present invention that the relative proportion of the non-aqueous phase in injectable emulsions be below about 25%.

On the other hand, compositions for topical administration should preferably be viscous, and to this end the relative proportion of the non-aqueous phase should preferably be above about 30%.

The preferred ranges of ingredients in injectable emulsion according to the invention are: oily carrier—about 3–20%, 6–10% being particularly preferred; phospholipids—about 0.5–3%, 0.75–2% being particularly preferred; cationic surfactants or lipids—0.05–2%, 0.1–0.4% being particularly preferred. Where the emulsion comprises a non-ionic surfactant its preferred range is about 0.5–3%. These preferred ranges are to be understood as standing each by itself and not cumulative.

A preferred pH in the aqueous phase of the emulsion of the invention is about 5.0–8.5, 6.0–8.0 being particularly preferred especially for parenteral administration.

The present invention also provides a pharmaceutical or a cosmetic composition which comprises an effective amount of a hydrophobic active ingredient, having pharmaceutical or cosmetic activity, as the case may be, and a carrier, being the above oil-in-water type emulsion.

Cosmetic compositions of the invention include various hair and body-care preparations, e.g. shampoos, body creams, sun-tan lotions, and the like. Such compositions may at times be supplemented with gel-forming polymers, in order to increase viscosity, as already pointed out above.

Cosmetically active hydrophobic active ingredients which may be incorporated into emulsions of the invention are, for example, anti-oxidants and anti-free radicals such as α-tocopherol; essential acids such as Complex Omega 6™ (manufactured by Seporga, Nice, France); sunscreen agents such as Parsol MCX™ or Parsol 1789™ (Givaudan, Switzerland).

Pharmaceutical compositions of the invention include parenteral, oral, ocular and topical composition. In parenteral and ocular compositions the aqueous phase is suitably saline or another isotonic solution. In oral compositions the aqueous phase may suitably be supplemented with flavouring agents to increase their platability. Ocular or topical compositions may in some cases be supplemented compositions of the invention.

Pharmaceutically active hydrophobic drugs which may be incorporated into emulsions of the invention include drugs for the treatment of glaucoma, anti-inflammatory drugs, antibiotic drugs, anti-cancer drugs, anti-fungal drugs and anti-viral drugs.

Examples of anti-glaucoma drugs are β-blockers such as timolol-base, betaxolol, atenolol, livobunolol, epinephrine, dipivalyl, oxonolol, acetazolamide-base and methzolamide.

Examples of anti-inflammatory drugs are steroidal drugs such as cortisone and dexamethasone and non-steroidal anti-inflammatory drugs (NSAID) such as piroxicam, indomethacin, naproxen, phenylbutazone, ibuprofen and diclofenac acid.

An example of an antibiotic drug is chloramphenicol. Examples of anti-fungal drugs are nystatin and miconazole. Examples of an anti-viral drug is Acyclovir™ (Boroughs-Welcome, U.K.). Examples of anti-allergic drugs are pheniramide derivatives.

It is generally preferred, in particular in emulsions intended for parenteral use, that the particles in the emulsion will have a diameter below about 1 μm, a diameter less than 0.5 μm being particularly preferred. Even more preferred are emulsions having a droplet size of below about 0.3 μm and even below about 0.2 μm. Small droplets are preferred also since submicron emulsions have a higher degree of stability, particularly during steam autoclaving. Furthermore, small droplets enable sterilization by filtration. However, emulsions with larger droplet size, above 1 μm, may at times be very useful for various purposes, such as in emulsions intended for topical or ocular applications and particularly for topical cosmetic applications.

The emulsion of the present invention may be prepared in a number of ways. By one way of preparation, an aqueous solution and an oily solution are first separately prepared. The non-ionic surfactant, the osmotic pressure regulator and the preservative (if present) are included in the aqueous solution, and the oil, the phospholipid, the hydrophobic drug, the cationic surfactant and, if present, also the antioxidant, in the oily solution. The phospholipids may also be dissolved in another, alcohol solution, which is mixed with the aqueous solution. The resulting aqueous-alcohol mixture is then heated until the alcohol evaporates and the phospholipids become dispersed in the aqueous solution.

The aqueous solution and the oily solution are then mixed with one another, preferably after each has been separately heated. However, the mixture thus obtained does not yet consist of sufficiently small droplets, the size of which (obtained after mixing, e.g. with a magnetic stirrer) is about 10 μm. The droplet size may then be decreased by the use of emulsification equipment, such as Ultra Turrax™ (Jenkle and Kunkel, Stauffen, Germany) which yields droplets having an average diameter of about 1.1 μm, or of a high shear mixer, e.g., Polytron™ (Kinematica, Lucerns, Switzerland) which yields droplets having an average diameter of about 06 μm.

Small droplets may be obtained when utilizing a two-stage pressure homogenizer, in which the crude dispersion is forced under high pressure through the annular space between a spring-loaded valve and then through the valve seat, the second stage being in tandem with the first so that the emulsion is subjected to two very rapid dispersion processes. Example of such an apparatus is the Gaulin™ homogenizer (A.P.V. Gaulin, Hilversum, The Netherlands or A.P.V. Rannie, Albertsland, Denmark). After homogenization in such an apparatus, the emulsion droplets have an average diameter of less than 0.3 μm, with a high degree of uniformity in droplet size. Even smaller droplets may be obtained when the emulsification process combines the use of a polytron-type high shear mixer followed by homogenization. The droplets which are obtained in such a combination have an average diameter of about 0.1–0.15 μm.

DESCRIPTION OF THE DRAWINGS

In the following descriptions reference will at times be made to the annexed drawings in which.

DESCRIPTION OF SPECIFIC EMBODIMENTS

Figure 1:
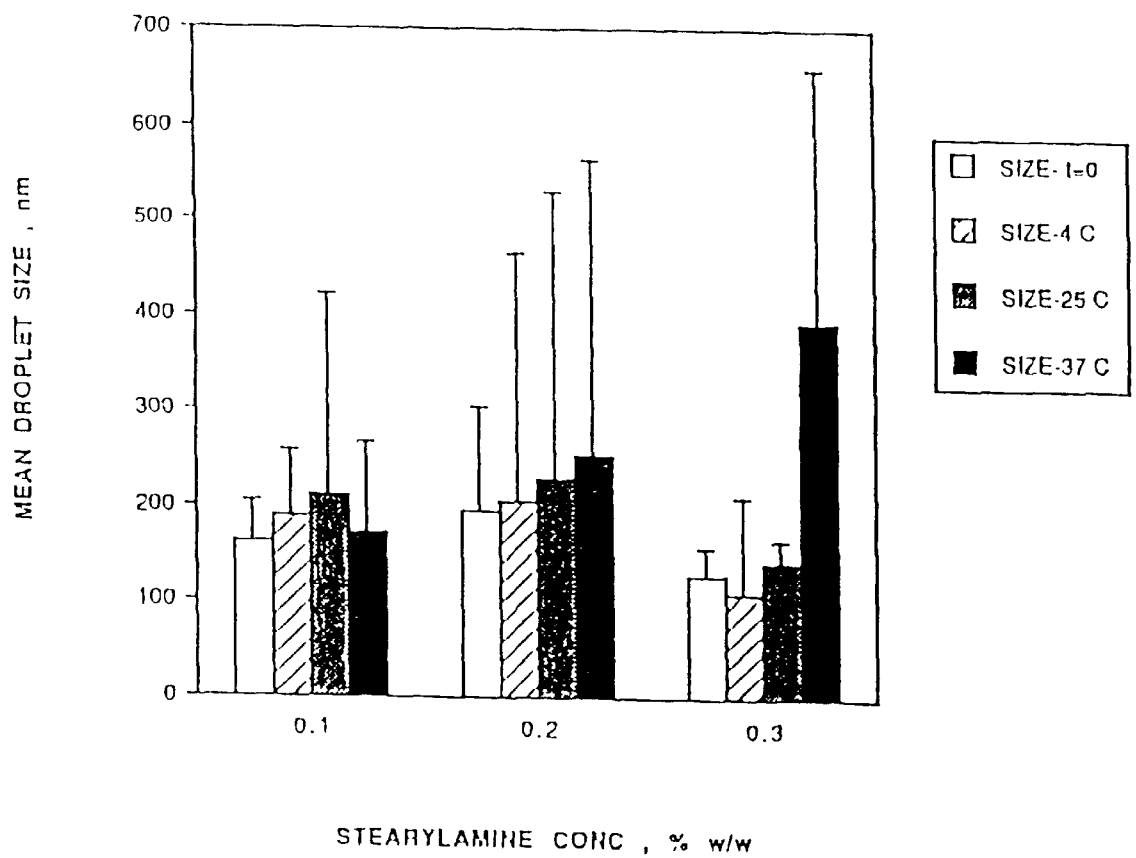
FIG. 1 shows the mean droplet size of emulsions with different concentrations of stearylamine at different temperatures following shaking at 100 rpm for 48 hrs.

The invention will be illustrated in the following by some non-limiting specific embodiments described in the examples below.

Example 1

Emulsion consisting of the following ingredients were prepared (% w/w):

MCT oil 8.0
Lipoid E-80™ 1.0
α-tocopherol 0.2
Pluronic F-68™ 2.0
stearylamine 0–0.4 glycerine 2.25
distilled water 100%

The preparation of the above emulsions was carried out as follows:

Aqueous, oily and alcohol solutions were separately prepared. The aqueous solution consisted of water, Pluronic F-68 and glycerine adjusted to pH 6.8; the oily solution consisted of MCT oil, stearylamine and α-tocopherol; the alcohol solution consisted of Lipoid E-80 (1 gm/10 ml). Each of the three solutions was filtered (TE and BA filter types, Schull & Schleicher, Dassel, Germany). The oily solution was heated to 70° C. The alcohol solution was mixed with the water solution and the combined alcohol-water solution was heated to 80° C. until all the alcohol evaporated. The two solutions were mixed and stirred with a magnetic stirrer and the resulting mixture was further heated to a temperature of 85° C. At this temperature the coarse emulsion which was obtained was further mixed by a high shear mixer Polytron™ for 3 minutes, and then rapidly cooled to below 20° C. After cooling, the emulsion was homogenized by a one-stage homogenizer (Rannie, Albertsland, Denmark) for 5 minutes at 10000 psi and then cooled again. After adjusting the pH to 6.8–7.0 the emulsion was filtered through a membrane filter (TE, Schull & Schleicher, having a pore size of 0.45 μm) and transferred to plastic bottles that were sealed under a nitrogen atmosphere.

The emulsions were sterilized by a steam autoclave at 121° C. for 15 minutes.

The mean particle size and the zeta potential were measured for each emulsion as follows:

(a) Particle size evaluation—The mean droplet size and size distribution were determined by means of a computerized laser light scattering apparatus (Coulter Counter Supernanosizer MD4™ Luton, U.K.). Each emulsion sample was diluted to the appropriate concentration with a filtered isotonic solution (2.5% w/v glycerol in water). The measurement was carried out at 25° C. Each emulsion system was analyzed twice, and for each diluted sample then size determinations were made.

(b) Zeta potential—The zeta potential was measured with a Malvern Zetasizer™ (Malvern, U.K.).

The results are shown in the following Table I:

TABLE I

| stearylamine conc. %, w/w | mean particle size, nm | zeta potential mV |
| --- | --- | --- |
| 0.0 | 136 | −14.60 |
| 0.1 | 151 | +8.51 |
| 0.2 | 139 | +14.91 |
| 0.3 | 144 | +20.91 |
| 0.4 | 143 | +21.80 |

As can be seen, while increasing stearylamine concentration did not cause a substantial change in the mean particle size, it had a profound affect on the zeta potential which changed from a negative zeta potential with no stearylamine to +21.8 with 0.4% stearylamine. Furthermore, as can be seen, there was no substantial increase in the zeta potential at a stearylamine concentration above 0.3%.

For comparison with the above emulsions, similar emulsions were prepared in which stearylamine was substituted with either Ovothin 200™, which comprises phospholipids which have substantially no charge; with Lipoid E-80™ which contains negatively charged phospholipids; or Lipoid E-75™ in which the phospholipids are somewhat less charged than in Lipoid E-80™. The comparison of the zeta potential obtained in these three emulsions with that obtained with the emulsions comprising stearylamine is shown in the following Table II:

TABLE II

| Emulsion (*) | Zeta potential (mV) |
| --- | --- |
| OV-200 | −5.62 |
| E-75 | −9.16 |
| E-80 | −14.64 |
| s.a - 0.1% | +8.51 |
| s.a - 0.2% | +14.91 |
| s.a - 0.3% | +20.91 |
| s.a - 0.4% | +21.80 |

(*) OV-200 = Ovothin 200 ™;
E-75 and E-80 = Lipoid E-75 ™ and E-80 ™;
s.a. = stearlyamine The above results clearly show that the stearylamine causes a reversal of the zeta potential from negative to positive. Furthermore, an increase in stearylamine concentration causes an increase in the zeta potential, although an increase above 0.3% had little effect.

Example 2

An emulsion consisting of the following ingredients was prepared (concentration in % w/w):

MCT oil 6.0
physostigmine 0.1
oleic acid 2.0
Lipoid E-80™ 1.0
α-tocopherol 0.02
Pluronic F-68™ 2.0
stearylamine 0.2
methyl paraben 0.2
butyl paraben 0.075
glycerine 2.250
distilled water to 100%

The emulsion was prepared in a similar manner to that of Example 1, with the aqueous solution consisting of distilled water, Pluronic F-68™ and glycerine, the remaining ingredients being included in the oily solution. Following filtration, the emulsions were sterilized by a two-stage membrane filtration, first filtration to a 0.45 μm followed by filtration through a 0.22 μm (both filters were TE, Schull & Schleicher).

The mean droplet size of this emulsion was measured in a similar manner to that described in Example 1 and was found to be 131 nm.

The zeta potential was measured using the moving boundary electrophoresis technique. The shape of the electrophoresis cell and the manner of converting electrophoretic ability dated to zeta potential have been described by Benita et al. (1986, Int. J. Pharm., 30, 47–55).

The zeta potential was found to be +5.7 mV.

Example 3

A similar emulsion to that described in Example 2 was prepared, with a physostigmine being replaced by 0.1% HU-211 (obtained from Professor R. Mechoulam, The Hebrew University of Jerusalem, Israel, (Refs. 7,8,9)). Following preparation, the pH of the emulsion was adjusted to about 6.8–7.0. The emulsion was sterilized by steam autoclave at 121° C. for 15 min.

This emulsion was found to have a mean droplet size of 131±87 nm and a zeta potential of +5.45 mV.

Example 4

An additional emulsion similar to that of Example 2 was prepared in which however the physostigmine was replaced with 1% pilocarpine. The pH of the emulsion was adjusted to 5.0 and the emulsion was sterilized by a two-stage filtration as described in Example 2.

The mean droplet size was found to be 103±27 nm and the zeta potential was found to be +8.63 mV.

Example 5

In a similar manner to that described in Example 1, an emulsion which had a higher oil concentration (20%) was prepared. The emulsion consisted of the following ingredients (concentration in % w/w):

MCT oil 20%
miconazole 1.0
Lipoid E-80™ 1.0
stearylamine 0.2
Pluronic F-68™ 2.0
glycerine 2.25
α-tocopherol 0.02
distilled water to 100%

The mean particle size of this emulsion was tested in the same manner as that described in Example 1 and was found to be 164±43 nm.

Example 6

A similar emulsion to that of Example 5 was prepared in which miconazole was replaced with 0.5% diazepam. In this emulsion the mean droplet size was found to be 151±65 nm.

Example 7

In a similar manner to that described in Example 1, an emulsion having the following ingredients was prepared:

MCT 8.0%
α-tocopherol 0.5
stearylamine 0.3
Pluronic F-68™ 2.0
glycerine 2.25
Lipoid E-80™ 1.0
distilled water to 100%

The mean droplet size was measured in the same manner as that described in Example 1 and was found to be 182±100 nm.

Example 8

The stability of an emulsion of Example 1 and similar emulsions having a different stearylamine concentration (0.1 and 0.3%) was tested. The stability test consisted of an accelerated test in which the emulsions were shaken at 100 rpm over 48 hours at different temperatures. The results are shown in FIG. 1.

It can be seen that the mean droplet size was moderately affected by the shaking at stearylamine concentrations of 0.1 and 0.2%. A slight increase in droplet size was noted as is reflected by the high values of a standard deviation which suggest a wider distribution of the droplet population. However, at 0.3% stearylamine there was no change either in the mean droplet size or the distribution in emulsions shaken at 4 and 25° C., while an increase was observed at 37° C.

Example 9

Figure 2:
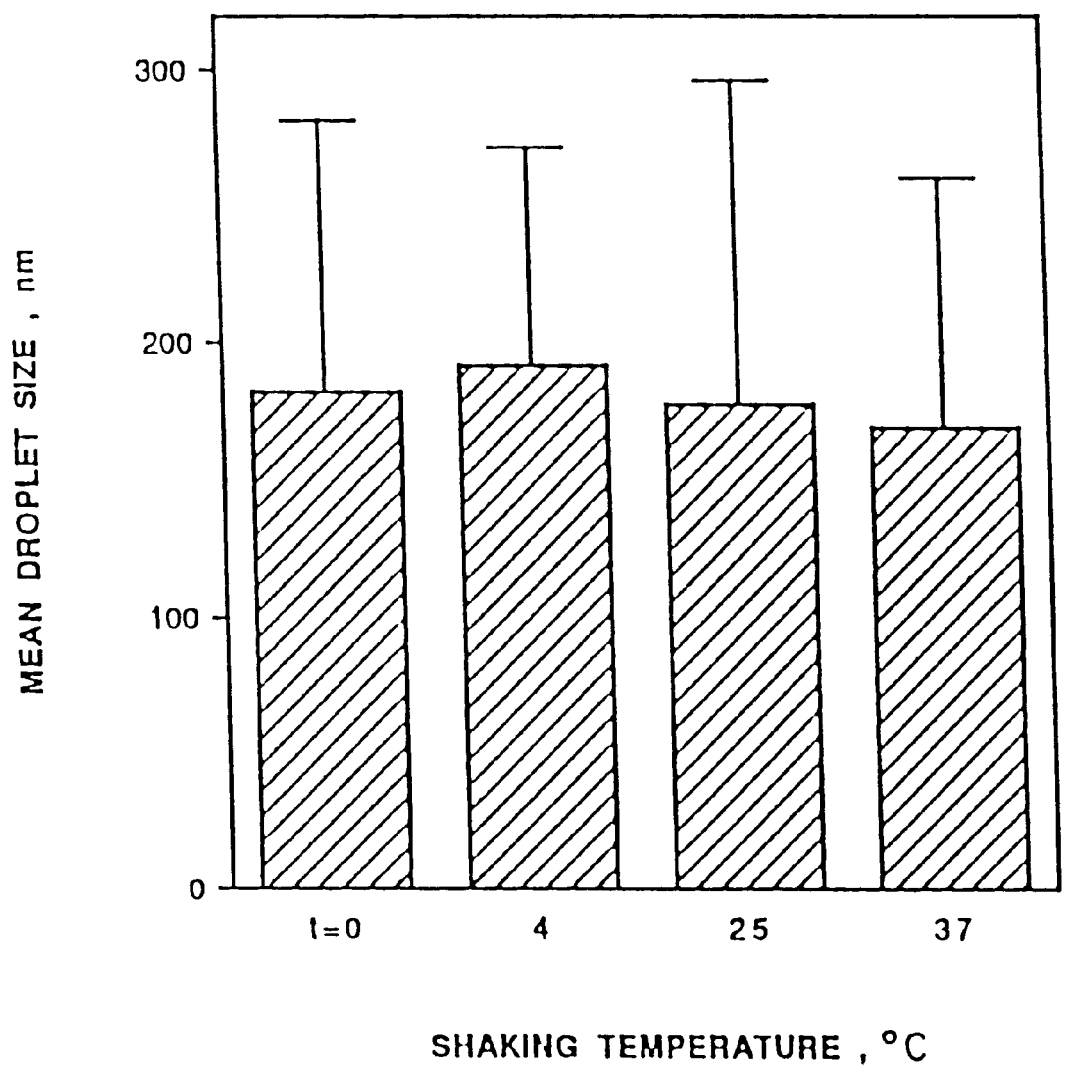
FIGS. 2 and 3 show the mean droplet size of emulsions prepared with either 0.3 or 0.2% stearylamine, respectively, after shaking (100 rpm) for 48 hours at various temperatures.
Figure 3:
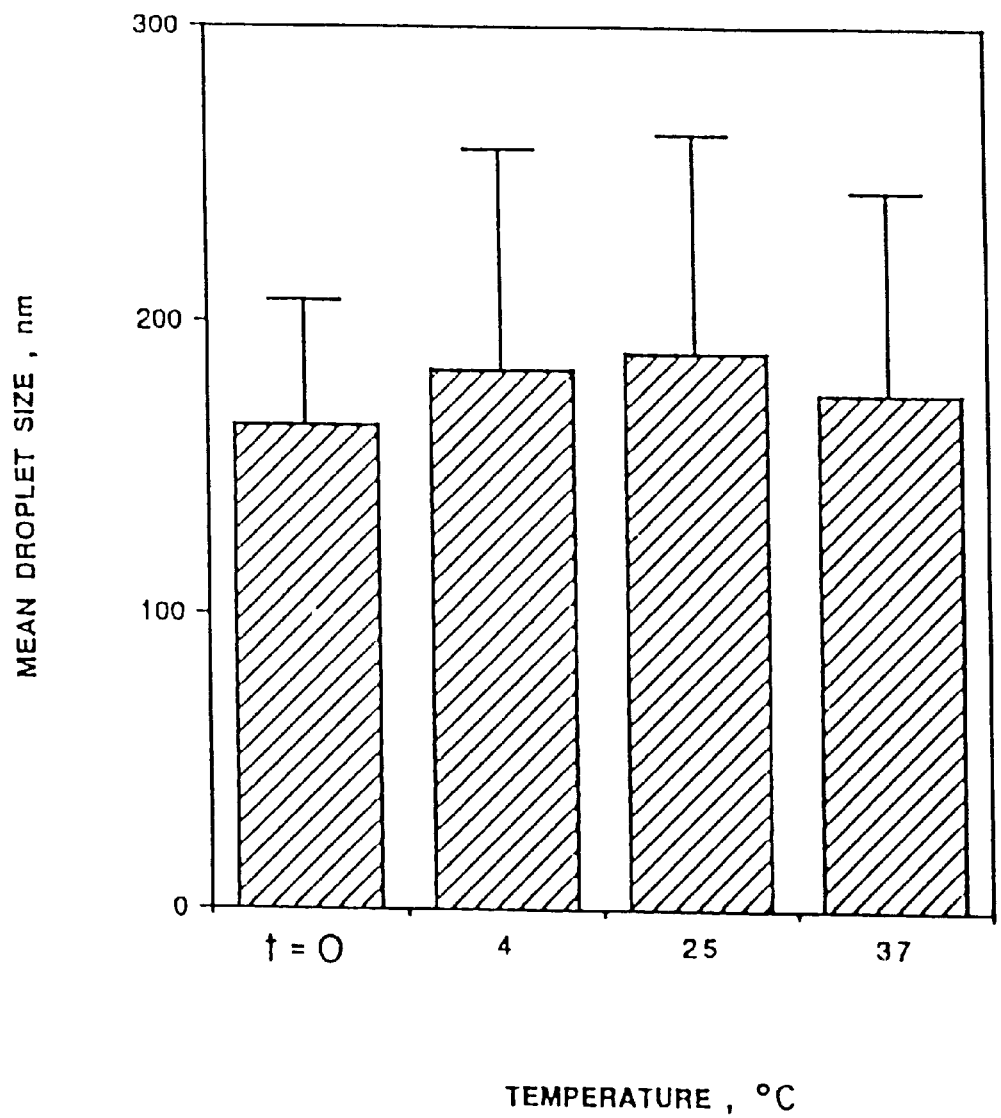

A similar experiment to that of Example 8 was conducted with the diazepam containing emulsion of Example 5 and with a similar emulsion prepared with 0.3% stearylamine and the results are shown in FIGS. 2 and 3, respectively.

The results demonstrate that there was essentially no change in mean droplet size following shaking at either of the temperatures.

Example 10

Figure 4:
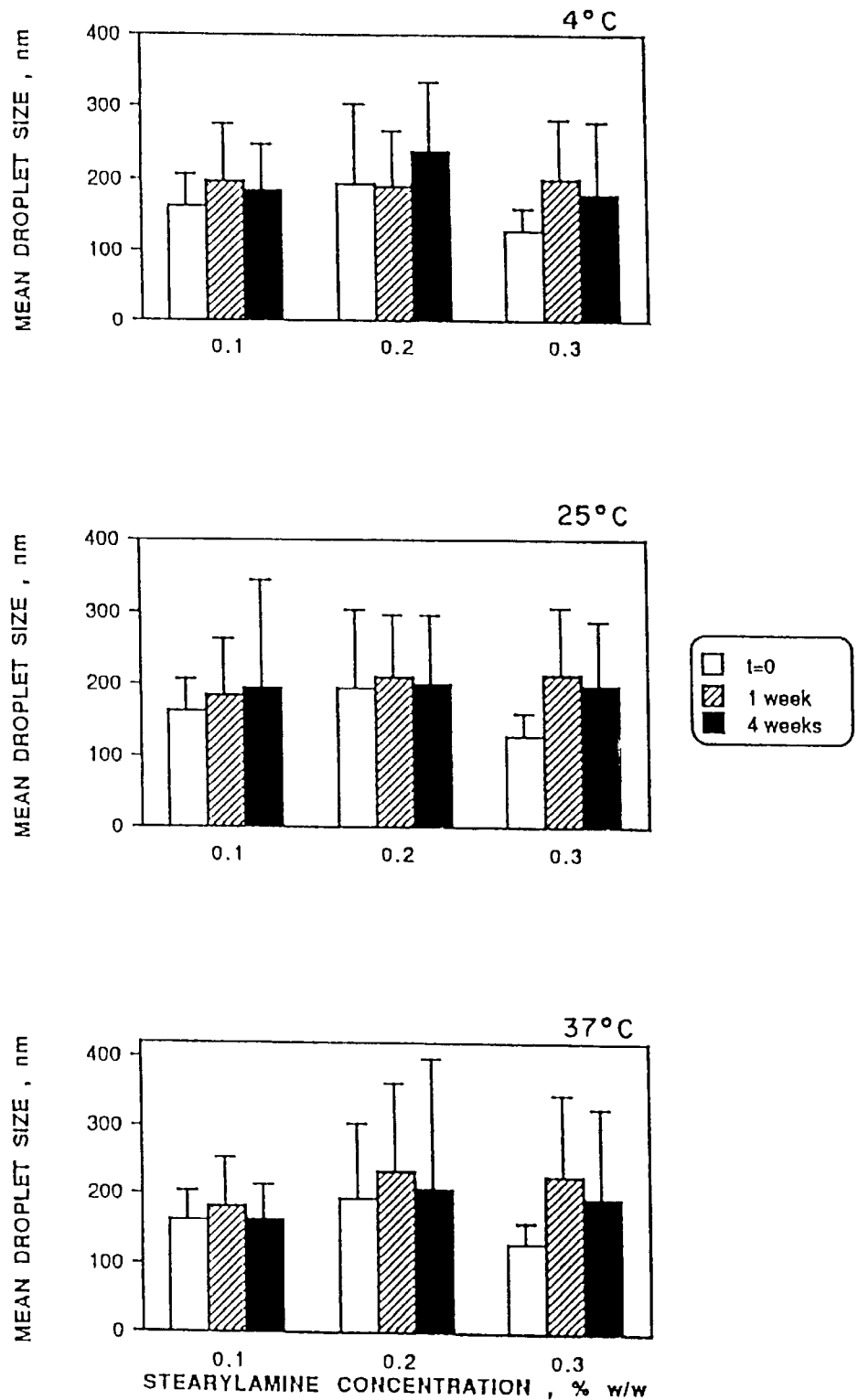
FIGS. 4a, 4b, and 4c show the mean droplet size of emulsions with various stearylamine concentrations after storage at various temperatures for 1 and 4 weeks.

The emulsion of Example 1 and similar emulsions with different concentrations of stearylamine (0.1 and 0.3%) were stored for 1 or 4 weeks at different temperatures (4° C., 25° C. and 37° C.) and the mean droplet size after these storage periods was tested. The results are shown in FIG. 4 and as can be seen, there is no substantial change in the mean droplet size even after storage at 37° C., in either of the three emulsions.

Example 11

Five different emulsions containing one or more of the following cosmetic active ingredients—Complex Omega 6™, α-tocopherol and ascorbic acid, were prepared.

The manner of preparation of the emulsions was similar to that described in Example 1 with the difference being in that the homogenization was with a two-stage homogenizer (Gaulin, APV, Hilversun, Holland) was for 4 min. at 8,000 psi and in that phospholipids were dissolved directly in the oil phase prior to homogenization. Following homogenization the pH of the emulsion was adjusted to 6.0 with 0.5 N HCl and the emulsion was filtered and transferred to plastic bottles under nitrogen atmosphere. A typical emulsion which was prepared ranges between 400 to 500 ml.

The ingredients of each emulsion and its pH (measured using a pH meter—Radiometer pH M63™, Copenhagen, Denmark) are showing the following Table III:

TABLE III

| comp. (% w/w) | EM-1 | EM-2 | EM-3 | EM-4 | EM |
|---|---|---|---|---|---|
| soybean oil | 8.0 | 8.0 | 8.0 | — | — |
| MCT oil | — | — | — | 5.0 | 5.0 |
| Omega 6 ™ | — | — | — | 3.0 | 3.0 |
| Lipoid E-80 | 1.0 | 1.0 | 1.0 | 1.0 | 1.0 |
| stearylamine | 0.3 | 0.3 | 0.3 | 0.3 | 0.3 |
| α-Tocopherol | 0.5 | 0.5 | 0.02 | 0.02 | 0.02 |
| Pluronic F-68 | 2.0 | 2.0 | — | 2.0 | — |
| glycerine | 2.25 | 2.25 | 2.25 | 2.25 | 2.25 |
| ascorbic acid | 0.1 | — | — | — | — |
| water to | 100.0 | 100.0 | 100.0 | 100.0 | 100.0 |
| pH | 6.53 | 6.71 | 6.10 | 7.30 | 7.26 |
| Sterilization by | autoclave | autoclave | — | * | * |

Various parameters of the emulsions were measured in a similar manner to that described in the previous examples. The results of the various analysis are shown in the following Table IV:

TABLE IV

| Test | EM-1 | EM-2 | EM-3 | EM-4 | EM-5 |
|---|---|---|---|---|---|
| Particle size (at t = 0) | 260 nm | 252 nm | 234 nm | 19 nm | 206 nm |
| Particle Size after 14 days | 315 nm | 379 nm | 228 nm | 217 nm | 227 nm |
|  | * | * | * |  |  |

TABLE IV-continued

| Test | EM-1 | EM-2 | EM-3 | EM-4 | EM-5 |
|---|---|---|---|---|---|
| Zeta potential (mV) | +37.21 | +41.48 | +39.47 | +13.0 | +37.93 |
| Accelerated stability (72 hours) | no creaming | some creaming | no creaming | no creaming | no creaming |
| Particle Size after Acceleration stability test | 290 nm * | 276 nm * | 247 nm | | |

* With two populations

Example 12

In order to confirm that the colloid particles are indeed positively charged, a selective absorption of two electrolytes—sodium thiocyanate and calcium chloride, was tested.

The emulsions of Example 1 with either 0.1, 0.2 or 0.3% stearylamine were used in this experiment and compared to an identical formulation which was prepared without stearylamine and was found by other tests to have negatively charged colloid particles (zeta potential of −14.64 mV).

Solutions of thiocyanate and of calcium chloride at concentrations of 2 and 1 mM respectively, were prepared. 15 ml of each one of these solutions were mixed with 15 ml of the emulsion resulting in diluted emulsion with a final thiocyanate or calcium chloride concentration of 1 and 0.5 mM, respectively. The thiocyanate diluted emulsion was allowed to stand for 1 hour at room temperature and then was filtered through an Amicon stirred filtration cell. The calcium chloride diluted emulsion was immediately immersed in the filtration cell and samples were ultrafiltered at given time intervals for 10 minutes over 1 hour.

The ultrafiltration was carried out as follows:
  YM-10, 62 mm Amicon ultrafiltration membranes (Amicon, Danvers, Mass., USA) were soaked in de-ionized water, with several changes of water, for at least 1 hour to remove water-soluble contaminants. The membranes were placed into a stirred filtration cell (Model 8200, Amicon, Danvers, Mass., USA) operated at room temperature. 30 ml of the diluted solution emulsion were placed into the stirred vessel and 20–40 psi of nitrogen were applied to begin filtration. Samples of approximately 1 ml of the filtrate were collected until 15–20% of the liquid was ultrafiltered. Each sample was then assayed for either thiocyanate using a colorimetric method described below, or for calcium chloride by atomic absorption technique.

Figure 5:
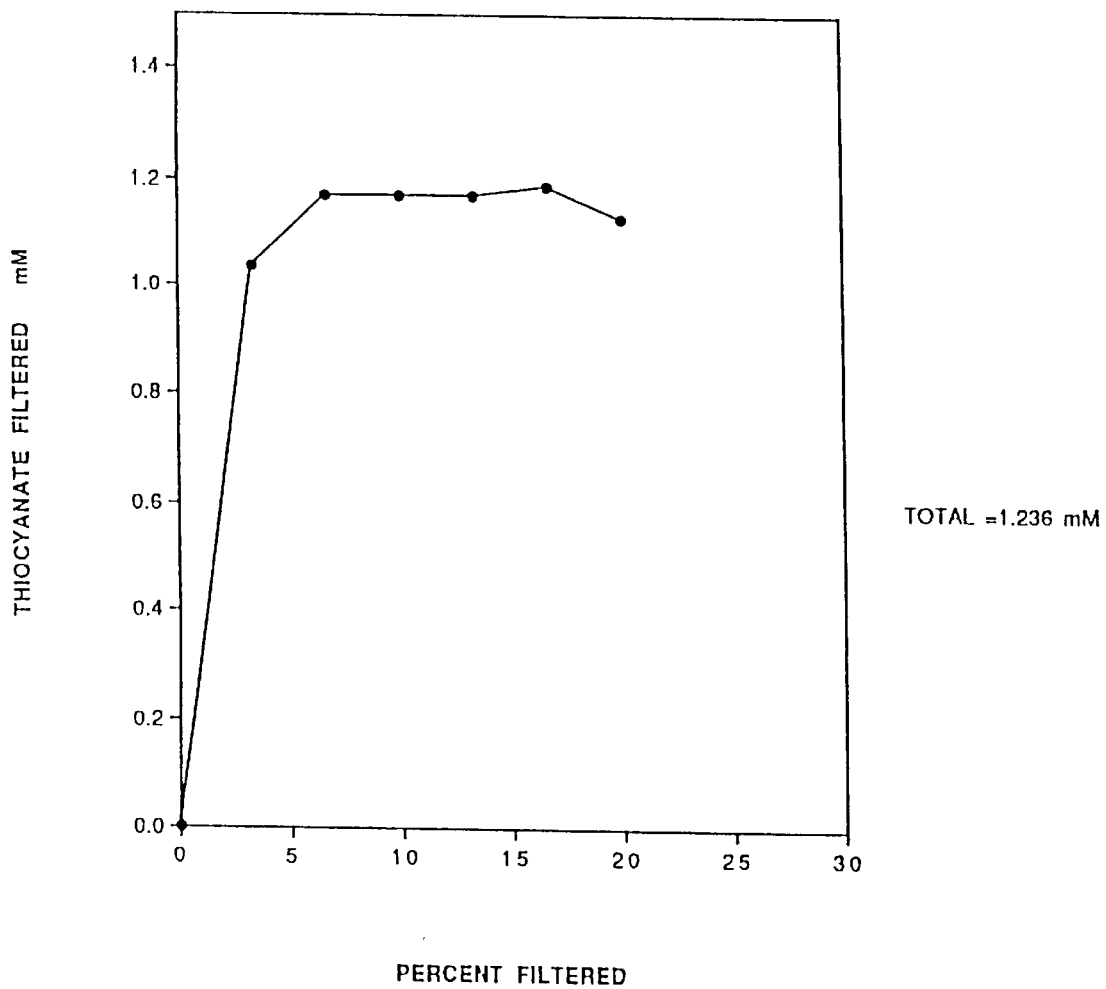
FIG. 5 shows the membrane recovery of aqueous thiocyanate solution at a concentration of 1 mM.

Prior to the use of the ultrafiltration technique to determine the selective potential absorption of thiocyanate and calcium, the technique required validation as already performed by others (see for example, Teagarden, D., Anderson, B. D. and Petre, W. J. Determination of the pH-dependent phase distribution of prostaglandin $E_1$ in a lipid emulsion by ultrafiltration. Pharm. Res. 5:482–487 1988). Membrane absorption and rejection have to be accounted for in order to accurately measure aqueous concentrations of thiocyanate or calcium. The ultrafiltration membranes were specifically selected for their exceptionally low non-specific binding. The effects of membrane binding and rejection of thiocyanate and calcium were studied by ultrafiltering and aqueous solution of sodium thiocyanate and calcium chloride at concentrations of 1.26 and 0.5 mM, respectively. The recovery curve of thiocyanate from the aqueous solution is shown in FIG. 5. The membrane appears to be nearly saturated after approximately 5–7% of the total volume has been filtered, as is evident in the levelling off of the curve. The percentage recovery was 96% of theoretical, indicating that rejection was negligible. Based on these rejection data, ultrafiltration data for thiocyanate solution and emulsion formulations required only a slight correction provided that at least 5% of the total volume was filtered to saturate the membrane. The recovery results for calcium showed that no calcium at all was absorbed by the membrane.

Thiocyanate Assay

Figure 6:
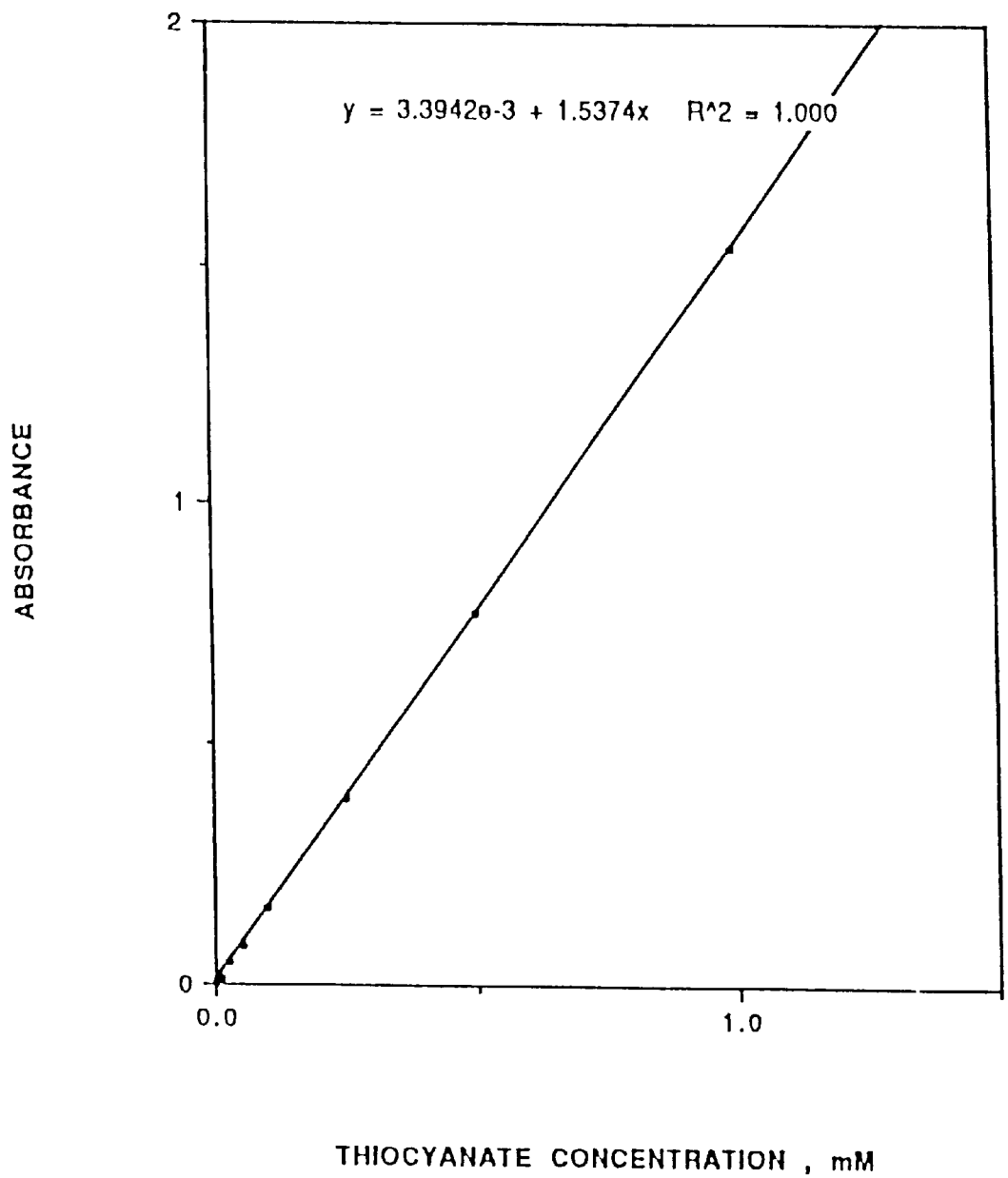
FIG. 6 shows a calibration curve of sodium thiocyanate at a concentration ranging from 0.01 to 1 mM.
Figure 7:
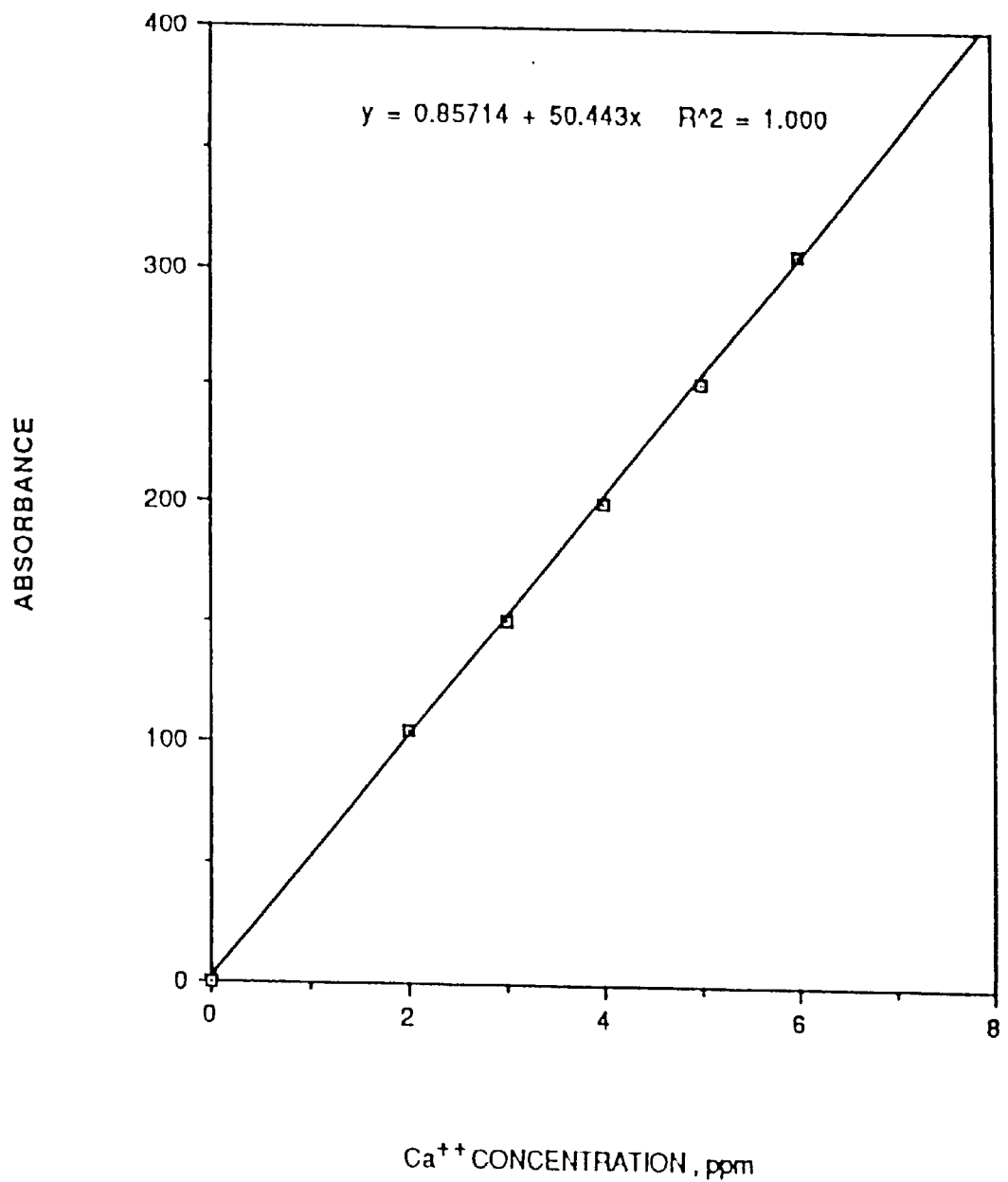
FIG. 7 shows a calibration curve of $Ca^{+2}$ at concentrations ranging from 0 to 6 ppm.

The method used for the thiocyanate assay was a modification of a well-established calorimetric reaction technique used for ferric chloride determination as described in Quantitative Chemical Analysis, I. M. Kolthoff, Macmillan Company, Toronto, Canada, 1969, 4th edition. 5 ml of ferric nitrate solution at a concentration of 0.01 M were added to one ml of unknown thiocyanate samples. Volume was adjusted to 10 ml with 1% nitric acid solution and the intensity of the orange color formed was immediately monitored at 480 nm and calculated against a calibration curve. A calibration curve was constructed using known concentrations of sodium thiocyanate ranging from 0.01 to 1 mM. A linear relationship was obtained, depicted in FIG. 6 with $r^2$ value of 1. The calcium concentration in the filtrates was measured using atomic absorption against a calibration curve after being calibrated with a standard solution of $Ca(NO_3)_2$. A linear relationship (FIG. 7) was observed over the range of $Ca^{++}$ concentrations from 0 to 6 ppm, achieved using 1% lanthanum oxide solution for appropriate dilution. Filtrate samples were diluted 1:5 with 1% lanthanum oxide solution prior to assay.

Figure 8:
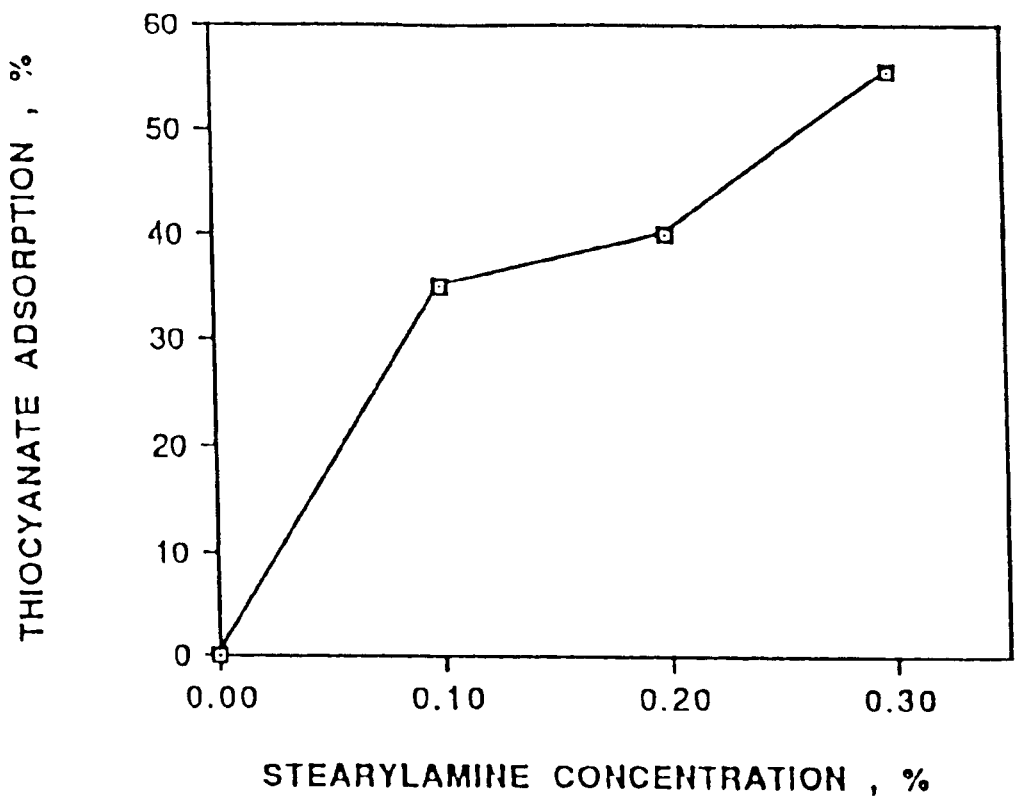
FIG. 8 shows thiocyanate absorption at different initial concentrations as a function of stearylamine concentration in the emulsion.

It can be noted that the negatively charged emulsion (0% stearylamine) did not absorb thiocyanate whereas an increase in absorption was noted with increasing stearylamine concentration (FIG. 8), suggesting that stearylamine conferred a positive charge to the emulsified droplets which interacted with the negative charge of thiocyanate. These results were clearly confirmed by the absorption studies of $CaCl_2$ which showed that the positively charged emulsion containing stearylamine did not absorb any $Ca^{++}$ while the negatively charged emulsion (0% stearylamine) absorbed 18% of the initial $Ca^{++}$ concentration.

These results emphasize the great advantage of the positively charged emulsions which are not sensitive to the presence of cationic electrolytes generally encountered in the physiological environment. In contrast to the negatively charged emulsions which separate upon addition of $Ca^{++}$, the positively charged emulsion's stability is not altered by the presence of these ions.

Example 13

In a similar manner to that described in Example 1, the following emulsion was prepared (concentration of the ingredients % w/w):

MCT 10.0
Lipoid E-80™ 1.0
Pluronic F-68™ 2.0
cholesteryl betainate 1.00
methyl paraben 0.10
butyl paraben 0.05
glycerine 2.25

α-tocopherol 0.02
distilled water to 100.0

The zeta potential which was measured by the moving boundary technique was found to be +15 mV and the mean droplet size measured in the same manner as that described in Example 1 was found to be 150 nm.

The above emulsion was modified by replacing the 1% cholesteryl betainate with 1.4% or 1.66% of the same ingredient. This yielded a zeta potential of +20 and +26 mV, respectively.

In order to show that the positive zeta potential is conferred by cholesteryl betainate, similar emulsions to the above were prepared in which the cholesteryl betainate was replaced with cholesteryl sulphate (negatively charged ester). In this case the zeta potential was found to be negative −20 mV.

The stability of the above cholesteryl betainate emulsion was tested in a similar manner to that described in the previous examples and the results are shown in the following Table V:

TABLE V

| | Mean droplet size (nm) | | | |
|---|---|---|---|---|
| | immediately following preparation | after autoclave | after shaking-100 hrs | after heating-4 days | after heating-14 days |
| Batch 1 | 140 | 102–52% 232–48% | 168 170 | 158 — | 150 — |
| Batch 2 | 167 | 170 | 179 | — | — |
| Batch 3 | 156 | 163 | — | — | — |

The above results clearly demonstrate the very good stability of emulsions of the invention.

The resistance of the cholesteryl betainate emulsion to the addition of cations was tested and compared to that of the above cholesteryl sulphate emulsion. The following results were obtained:

1. No change with respect to particle size was observed with cholesteryl betainate emulsions after the addition of calcium chloride (3 mM—5 days; 5 mM—2 hrs.) or sodium citrate (50 mM—2 Hrs.).

2. A marked degradation of cholesteryl sulphate emulsion was noted, as evidenced by a considerable increase in particle size, upon addition of sodium citrate (50 mM—2 hrs.) or calcium chloride (5 mM—2 hrs.)

The same experiment was repeated also with the commercially available emulsion Intralipid™ (manufactured by Kabi-Vitrum, Sweden) and this emulsion was shown to be destroyed by the addition of 3 mM or 5 mM calcium chlorides.

The above results clearly demonstrate the resistivity of the emulsion of the invention to cations present in the surrounding medium. Against this, despite the positive charge of the particles, there was no selective absorption of the negatively charged citrate anions.

Example 14

27 different emulsions containing Parsol MCX™ (Givaudan, Switzerland) were prepared. The ingredients of each emulsion is shown in the following Table VI:

TABLE VI

| COMPOSITION (% w/w) | AS2 | AS3 | AS4 | AS5 | AS6 | AS7 | AS8 | AS9 | AS10 | AS11 | AS12 | AS13 |
|---|---|---|---|---|---|---|---|---|---|---|---|---|
| MCT | 15 | 15 | 15 | 15 | 15 | 15 | 15 | 15 | — | 15 | — | — |
| Isopropyl palmitate | — | — | — | — | — | — | — | — | — | — | 15 | — |
| Silicone oil | — | — | — | — | — | — | — | — | — | — | — | 15 |
| Paraffin oil | — | — | — | — | — | — | — | — | — | — | — | — |
| Miglyol | — | — | — | — | — | — | — | — | — | — | — | — |
| Parsol MCX | 5 | 5 | 5 | 5 | 5 | 5 | 5 | 5 | 5 | 5 | 5 | 5 |
| Lipoid E-80 | 1 | 1 | 1 | 1 | — | — | — | — | 1 | 1 | 1 | 1 |
| Lipoid E-75 | — | — | — | — | 1 | 1 | — | — | — | — | — | — |
| PC | — | — | — | — | — | — | 1 | 1 | — | — | — | — |
| Stearylamine | 0.3 | 0.3 | 0.3 | 0.3 | 0.3 | 0.3 | 0.3 | 0.3 | 0.3 | 0.3 | 0.3 | 0.3 |
| α-Tocopherol | 0.02 | 0.02 | 0.02 | 0.02 | 0.02 | 0.02 | 0.02 | 0.02 | 0.02 | 0.02 | 0.02 | 0.02 |
| Poloxamer 188 | 2 | — | 1 | 1.5 | 2 | — | 2 | — | 2 | 3 | 2 | 2 |
| Glycerine | 2.25 | 2.25 | 2.25 | 2.25 | 2.25 | 2.25 | 2.25 | 2.25 | 2.25 | 2.25 | 2.25 | 2.25 |
| Water to | 100 | 100 | 100 | 100 | 100 | 100 | 100 | 100 | 100 | 100 | 100 | 100 |

| COMPOSITION (% w/w) | AS14 | AS15 | AS16 | AS17 | AS18 | AS19 | AS20 | AS21 | AS22 | AS23 | AS24 | AS25 |
|---|---|---|---|---|---|---|---|---|---|---|---|---|
| MCT | — | — | — | 17.5 | 17.5 | 10 | 10 | — | — | — | 15 | 15 |
| Isopropyl palmitate | — | — | — | — | — | — | — | 15 | — | — | — | — |
| Silicone oil | — | — | — | — | — | — | — | — | — | 15 | — | — |
| Paraffin oil | 15 | — | — | — | — | — | — | — | 15 | — | — | — |
| Miglyol | — | 15 | 15 | — | — | — | — | — | — | — | — | — |
| Parsol MCX | 5 | 5 | 5 | 2.5 | 2.5 | 10 | 10 | 5 | 5 | 5 | 5 | 5 |
| Lipoid E-80 | 1 | 1 | 1 | 1 | 1 | 1 | 1 | 1 | 1 | 1 | 1 | 1 |
| Lipoid E-75 | — | — | — | — | — | — | — | — | — | — | — | — |
| PC | — | — | — | — | — | — | — | — | — | — | — | — |
| Stearylamine | 0.3 | 0.3 | 0.3 | 0.3 | 0.3 | 0.3 | 0.3 | 0.3 | 0.3 | 0.3 | 0.3 | 0.3 |
| α-Tocopherol | 0.02 | 0.02 | 0.02 | 0.02 | 0.02 | 0.02 | 0.02 | 0.02 | 0.02 | 0.02 | 0.02 | 0.02 |
| Poloxamer 188 | 2 | 2 | — | 2 | — | 2 | — | — | — | — | 2 | 2 |
| Glycerine | 2.25 | 2.25 | 2.25 | 2.25 | 2.25 | 2.25 | 2.25 | 2.25 | 2.25 | 2.25 | 5 | 7.5 |
| Water to | 100 | 100 | 100 | 100 | 100 | 100 | 100 | 100 | 100 | 100 | 100 | 100 |

Medium chain triglycerides (MCT) were obtained from Societe Industrielle des Oleagineux St. Laurent (Blangy, France). Lipoid E-80™, E-75™ and PC (phosphatidylcholine) were purchased from Lipoid (Ludwigshafen, FRG). Stearlyamine, Alpha-tocopherol and glycerin were purchased from Sigma (St. Louis, Mo., USA). Miglyol 112 was purchased from Dynamit Novel (Sweden). Paraffin, silicone oil and isopropyl palmitate were in compliance with CTFA (Cosmetic Ingredient Directory of Cosmetic Toiletry and Fragrances Association) specifications.

The emulsion was prepared essentially in the same manner to that described in Example 11.

Various properties of the emulsions were tested immediately after preparation or following a short term accelerated test (e.g. shaking over 48 hours at 100 rpm, excessive heating, sterilization by autoclave at 121° C. for 15 mins, centrifugation at 200 rpm). The properties included particle size evaluation and a zeta potential (in the manner described in Example 1), and the degree of creaming (by visual observation).

The effect of the following parameters was investigated:
1. Effect of poloxamer concentration.
2. Effect of pH.
3. Effect of the concentration of the actual principal Parsol MCX.
4. Effect of relative PE (phosphatidylethanolamine) content.
5. Effect of oil nature.
6. Effect of glycerin content.

Effect of Poloxamer Concentration

The effect of poloxamer concentration on the physicochemical properties of the emulsion is shown in Table VII below.

As can be noted from Table VII, the variation in poloxamer concentration moderately affected zeta potential, while is markedly affected particle size distribution—increasing poloxamer concentration generally causes a decrease in particle size.

Figure 9:
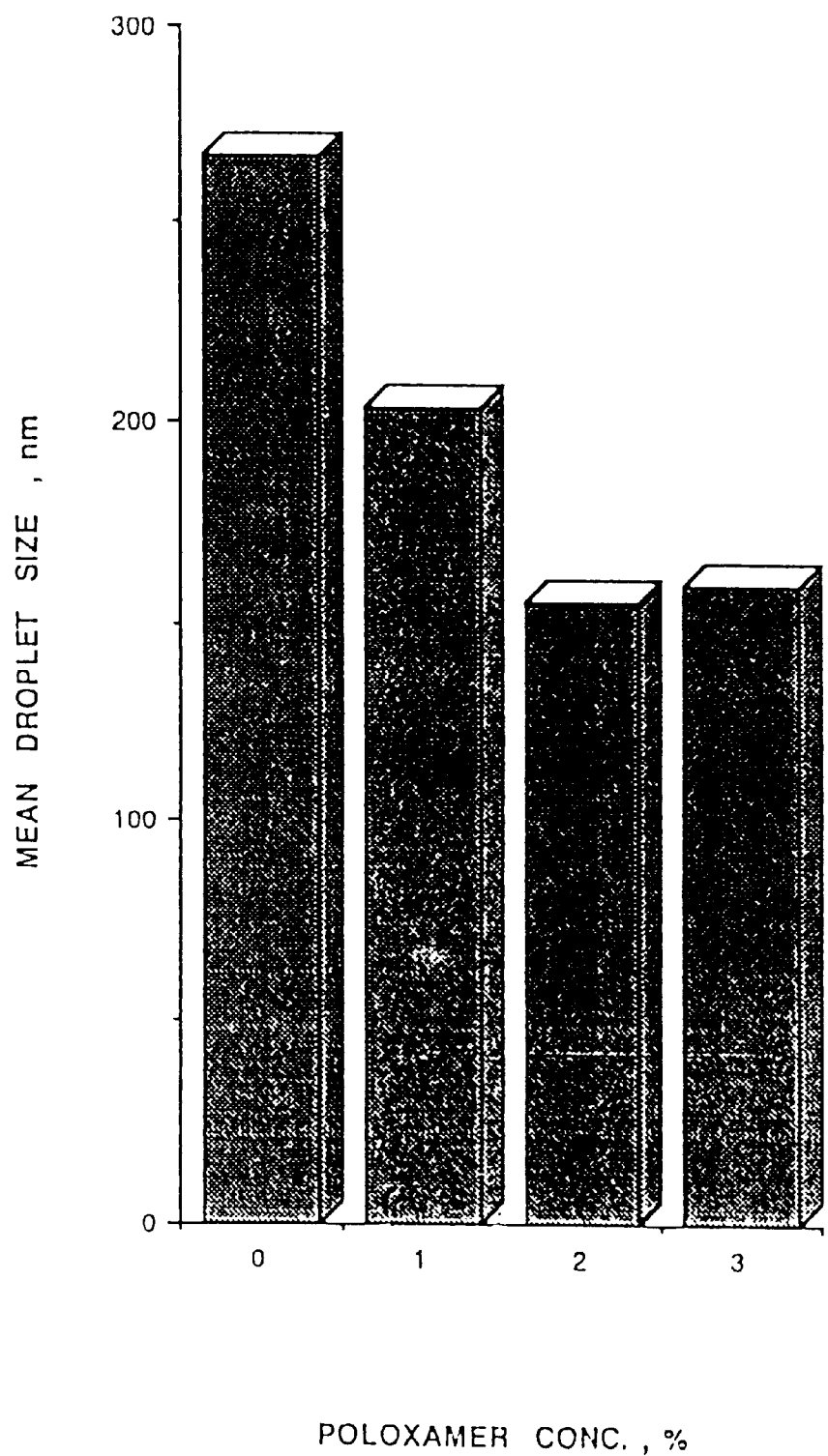
FIG. 9 shows the mean droplet size as a function of the poloxamer concentration.

As can further be seen from the results in Table X below, the presence of poloxamer effected the physicochemical properties of the emulsions. Poloxamer significantly decreased the droplet size profile of the emulsion and the zeta potential compared to emulsions without poloxamer. The effect of poloxamer concentration on the mean droplet size of the emulsions is shown in FIG. 9. It can clearly be seen that an increasing poloxamer concentration decrease the emulsions' droplet size. This gradual decrease behavior likely reflects the formation of a better close-packed mixed film of the emulsifying agents at the oil-water interface of the emulsion droplets.

TABLE VII

| Poloxamer conc. | Code name | Zp. (+mV) | PSD (nm) | | PSD after shaking (nm) | | | PSD after heating (nm) | | | PSD 2 weeks 37 C. (nm) | |
|---|---|---|---|---|---|---|---|---|---|---|---|---|
| 0.0 | AS3 | 46.29 | 267 ± 45 | | | 273 ± 65 | | 1. | 225 ± 70 | 63% | phase separator | |
| 0.0 | AS3–6 | 52.99 | 284 ± 61 | 1. | 135 ± 16 | 32% | 1. | 527 ± 61 | 37% | 1. | 150 ± 36 | 32% |
| | | | | 2. | 370 ± 97 | 68% | | 302 ± 59 | | 2. | 345 ± 100 | 68% |
| 1.0 | AS4 | 35.08 | 203 ± 90 | 1. | 176 ± 47 | 49% | 1. | 201 ± 24 | 29% | | 245 ± 96 | |
| | | | | 2. | 659 ± 150 | 51% | 2. | 812 ± 180 | 71% | | | |
| 1.5 | AS5 | 43.65 | 1. 191 ± 47 88% | 1. | 133 ± 16 | 27% | 1. | 164 ± 43 | 88% | | 185 ± 59 | |
| | | | 2. 711 ± 59 12% | 2. | 734 ± 88 | 73% | 2. | 1280 ± 300 | 12% | | | |
| 2.0 | AS2 | 42.72 | 156 ± 39 | | 159 ± 37 | | | 159 ± 56 | | | 190 ± 83 | |
| 3.0 | AS11 | 45.2 | 160 ± 61 | | 145 ± 50 | | 1. | 137 ± 27 | 95% | | 148 ± 35 | |
| | | | | | | | 2. | 1470 ± 420 | 5% | | | |

ZP - Zeta Potential
PSD - Particle Size Distribution

Effect of pH

The effect of pH variation on the zeta potential of emulsion AS2 (with poloxamer) and emulsion AS3 (without poloxamer), as shown in the following Tables VIII and IX, respectively.

TABLE VIII

| | | Zeta potential (+mV) | |
|---|---|---|---|
| pH Initial | Actual pH (6 w)[1] | average | STD[2] |
| 5.09 | 4.83 | 33.83 | 7.03 |
| 6.00 | 5.21 | 42.72 | 1.58 |
| 7.00 | 5.92 | 42.38 | 3.34 |
| 7.93 | 6.65 | 37.06 | 4.92 |
| 9.05 | 7.76 | 45.37 | 1.17 |

[1]After 6 weeks' storage
[2]STD - Standard deviation

TABLE IX

| | | Zeta potential (+mV) | |
|---|---|---|---|
| pH Initial | Actual pH (6 w)[1] | average | STD[2] |
| 3.09 | 3.31 | 49.05 | 0.33 |
| 4.98 | 4.76 | 38.70 | 2.94 |
| 6.00 | 5.21 | 46.29 | 0.62 |
| 6.98 | 5.60 | 49.19 | 1.22 |
| 8.93 | 6.28 | 50.60 | 3.14 |

[1]After 6 weeks' storage
[2]STD - Standard deviation

It can be seen that the pH varied with time mainly in the alkaline range.

After 6 weeks storage at room temperature, irrespective of the initial or actual pH, there was no marked change in the zeta potential value (results not shown).

The pKa of stearylamine is 10.60 and accordingly it was expected that the change in pH from 3 to 9 would not alter the dissociation of this molecule.

Figure 10A:
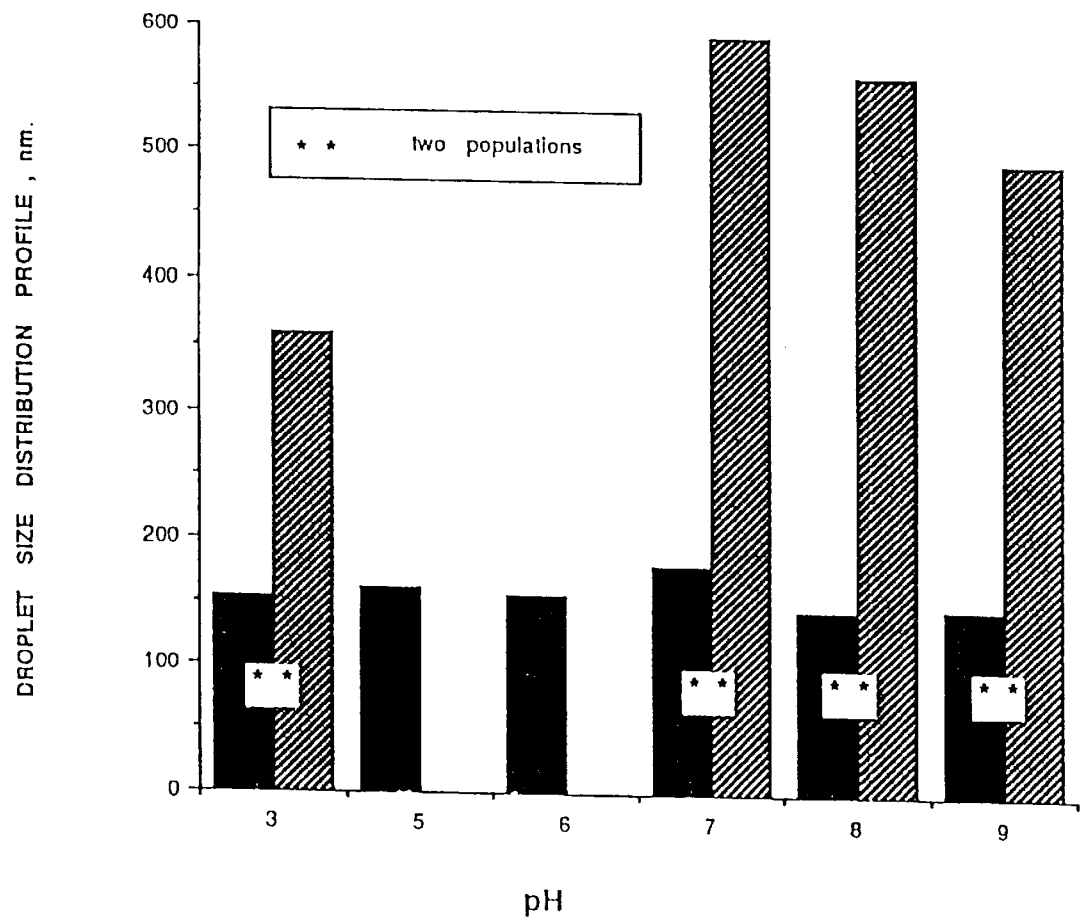
FIGS. 10a and 10b show the effect of pH on the droplet size distribution profile of an emulsion prepared with poloxamer (a) or without poloxamer (b).
Figure 10B:
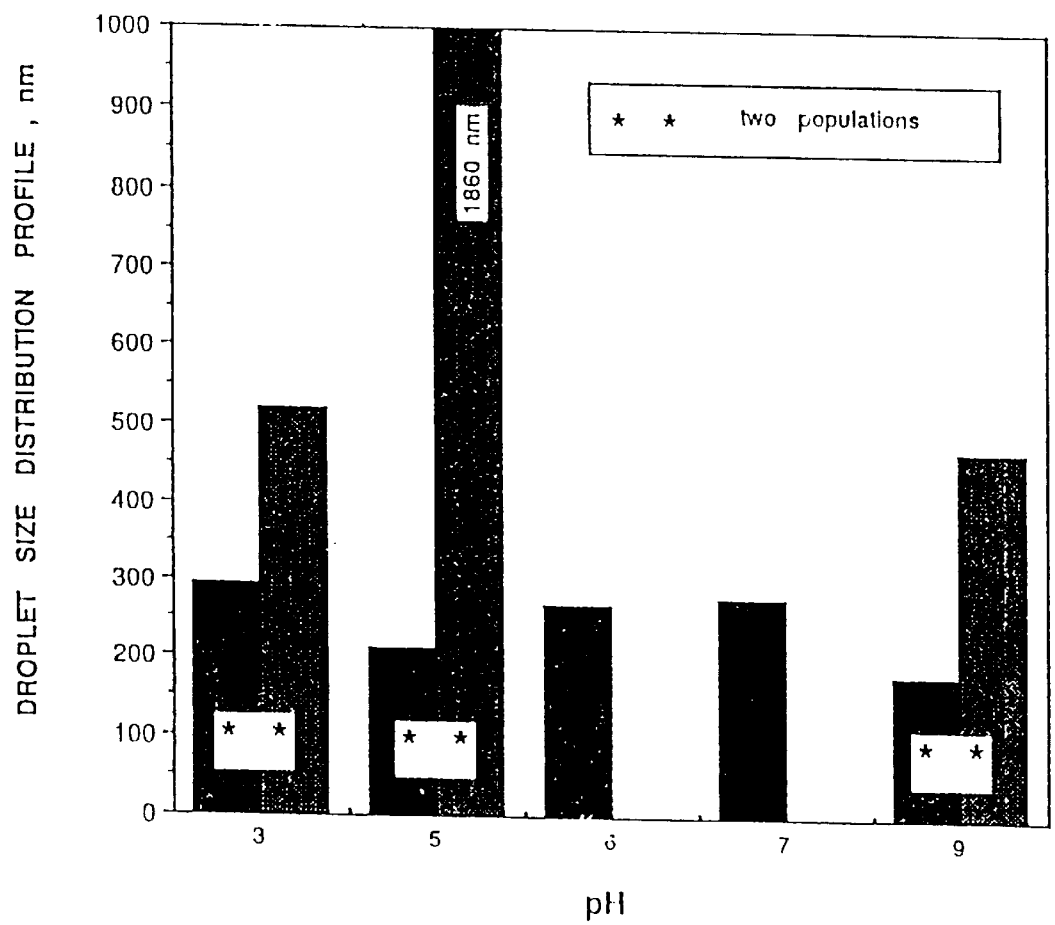

The effect of a change in pH on particle size distribution of emulsion AS2 (with poloxamer) and emulsion AS3 (without poloxamer) measured one day after preparation is shown in FIGS. 10a and 10b, respectively. As can be seen in these figures, the variation in pH had essentially no or very little effect on the average droplet size of the small-droplet population. As can be seen in most of the tested emulsions, two distinct populations of droplets were observed with a mean droplet size varying between 200 to 1000 nm. A homogeneous population of droplets was observed between pH 5 to 6 to 7 for emulsions AS2 and AS3, respectively.

Effect of Parsol MCX Concentration

The effect of Parsol MCX concentration on the physico-chemical properties of the emulsions prepared with and without poloxamer is shown in Table X below. Two sets of emulsions were prepared with and without poloxamer. In the same series of experiment, there was essentially no effect of Parsol MCX on the various emulsions' properties indicating that this active principle does not interfere with the oil-in-water interface.

that PE are negatively charged, it would have been expected that with the increase PE content in the phospholipid preparation, the zeta potential would decrease, but the result shown in Table XI below, show that the opposite trend: namely, the lowest zeta potential was observed with the PC phospholipid formulation which does not contain PE.

TABLE XI

| PL (PE content) % | Code name | Pol. | Zp. (+mV) |
|---|---|---|---|
| E-80 (8–11%) | AS2 | + | 42.72 |
| E-80 (8–11%) | AS3–6 | − | 52.99 |
| E-75 (15–18%) | AS6 | + | 49.18 |
| E-75 (15–18%) | AS7 | − | 47.47 |
| PC (0%) | AS8 | + | 37.64 |
| PC (0%) | AS9 | − | 34.78 |

PL - Phospholipids
Pol - Poloxamer
Zp - Zeta potential

Effect of Oil Nature

As can be seen in Table XII below, the zeta potential was not altered by the oily nature. However, changing the oil

TABLE X

| Parsol conc. | Code name | Pol. | Zp. (+mv) | PSD (nm) | | | PSD after shaking (nm) | | | PSD after heating (nm) | | | PSD 2 week 37 C. (nm) | | |
|---|---|---|---|---|---|---|---|---|---|---|---|---|---|---|---|
| 2.5 | AS17 | + | 37.46 | 198 ± 130 | | | 1. | 169 ± 43 | 33% | 1. | 147 ± 33 | 97% | 1. | 193 ± 86 | 90% |
|  |  |  |  |  |  |  | 2. | 706 ± 120 | 67% | 2. | 1630 ± 320 | 3% | 2. | 4220 ± 490 | 10% |
| 2.5 | AS18 | − | 47.56 | 1. | 288 ± 76 | 60% | 1. | 303 ± 93 | 51% | | 279 ± 73 | | 1. | 48 ± 12 | 8% |
|  |  |  |  | 2. | 806 ± 200 | 40% | 2. | 723 ± 96 | 49% |  |  |  | 2. | 598 ± 180 | 92% |
| 5.0 | AS2 | + | 42.72 | 156 ± 39 | | | | 159 ± 37 | | | 159 ± 56 | | | 190 ± 83 | |
| 5.0 | AS3–6 | − | 52.99 | 284 ± 61 | | | 1. | 135 ± 16 | 32% | | 302 ± 59 | | 1. | 150 ± 36 | 32% |
|  |  |  |  |  |  |  | 2. | 370 ± 97 | 68% |  |  |  | 2. | 345 ± 100 | 68% |
| 10.0 | AS19 | + | 46.95 | 166 ± 58 | | | 1. | 157 ± 40 | 82% | | 167 ± 64 | | 1. | 86 ± 10 | 14% |
|  |  |  |  |  |  |  | 2. | 1520 ± 370 | 12% |  |  |  | 2. | 322 ± 43 | 86% |
| 10.0 | AS20 | − | 49.47 | 413 ± 100 | | | 1. | 155 ± 40 | 26% | 1. | 196 ± 56 | 41% | 1. | 205 ± 24 | 19% |
|  |  |  |  |  |  |  | 2. | 826 ± 190 | 74% | 2. | 581 ± 170 | 59% | 2. | 755 ± 88 | 81% |

Pol. - Poloxamer
Zp - Zeta potential
PSD - particle size distribution

Effect of Relative PE Content

The PE contents in the 3 phospholipid preparations used varies: P-75—15–18%; E-80—8–11%; PC—0%. Seeing from MCT to any other oil type, dramatically decreased the stability of the emulsion.

TABLE XII

| Oil | Code name | Pol | Zp. (+mv) | PSD (nm) | | | PSD after shaking (nm) | | | PSD after heating (nm) | | | PSD 2 week 37 C. (nm) | | |
|---|---|---|---|---|---|---|---|---|---|---|---|---|---|---|---|
| MCT | AS2 | + | 42.72 | 156 ± 39 | | | | 159 ± 37 | | | 159 ± 56 | | | 190 ± 83 | |
| MCT | AS3–6 | − | 52.99 | 284 ± 61 | | | 1. | 135 ± 16 | 32% | | 302 ± 59 | | 1. | 150 ± 36 | 32% |
|  |  |  |  |  |  |  | 2. | 370 ± 97 | 68% |  |  |  | 2. | 345 ± 100 | 68% |
| Miglyol | AS15 | + | 45.15 | 189 ± 120 | | | 1. | 126 ± 50 | 56% | 1. | 160 ± 42 | 95% | | 167 ± 43 | |
|  |  |  |  |  |  |  | 2. | 352 ± 130 | 44% | 2. | 5150 ± 130 | 5% |  |  |  |
| Miglyol | AS16 | − | 45.88 | 1. | 175 ± 43 | 18% | 1. | 313 ± 56 | 85% | 1. | 183 ± 73 | 38% | 1. | 197 ± 79 | 51% |
|  |  |  |  | 2. | 874 ± 220 | 82% | 2. | 1420 ± 370 | 15% | 2. | 481 ± 78 | 62% | 2. | 453 ± 81 | 49% |
| Paraffin oil | AS14 | + | 46.87 | 155 ± 69 | | | 1. | 146 ± 44 | 77% | | 168 ± 86 | | 1. | 131 ± 16 | 92% |
|  |  |  |  |  |  |  | 2. | 482 ± 57 | 23% |  |  |  | 2. | 1030 ± 220 | 8% |
| Paraffin oil | AS22 | − | 44.04 | 1. | 131 ± 16 | 13% | | 698 ± 280 | | 1. | 223 ± 48 | 14% | 1. | 102 ± 27 | 7% |
|  |  |  |  | 2. | 763 ± 88 | 87% |  |  |  | 2. | 758 ± 88 | 86% | 2. | 797 ± 160 | 93% |
| Silicone oil | AS13 | + | 48.09 | 1. | 138 ± 22 | 62% | 1. | 125 ± 32 | 42% | 1. | 178 ± 49 | 82% | 1. | 131 ± 16 | 64% |
|  |  |  |  | 2. | 812 ± 180 | 38% | 2. | 741 ± 88 | 58% | 2. | 1780 ± 210 | 18% | 2. | 1070 ± 200 | 36% |
| Silicone oil | AS23 | − | 48.17 | 1. | 133 ± 16 | 42% | | 293 ± 55 | | | 286 ± 59 | | 1. | 135 ± 16 | 27% |
|  |  |  |  | 2. | 536 ± 120 | 58% |  |  |  |  |  |  | 2. | 693 ± 130 | 73% |
| Isopropyl Palmitate | AS12 | + | 37.55 | 149 ± 45 | | | 1. | 247 ± 64 | 71% | 1. | 197 ± 39 | 89% | 1. | 170 ± 43 | 61% |
|  |  |  |  |  |  |  | 2. | 1500 ± 370 | 29% | 2. | 750 ± 88 | 11% | 2. | 651 ± 150 | 39% |

TABLE XII-continued

| Oil | Code name | Pol | Zp. (+mv) | PSD (nm) | | | PSD after shaking (nm) | | | PSD after heating (nm) | | | PSD 2 week 37 C. (nm) | | |
|---|---|---|---|---|---|---|---|---|---|---|---|---|---|---|---|
| Isopropyl Palmitate | AS21 | – | An emulsion having the consistency of a cream was obtained which separated into two phases at room temperature after 48 hours | | | | | | | | | | | | |
| No oil Parsol-MCX only | AS10 | + | 48.56 | 1. 2. | 286 ± 59 1450 ± 370 | 45% 55% | 1. 2. 3. | 53.4 ± 13 270 ± 87 2180 ± 570 | 7% 53% 47% | 1. 2. | 251 ± 65 1780 ± 210 | 33% 67% | 1. 2. | 166 ± 43 1720 ± 220 | 65% 35% |

Pol - Poloxamer;
Zp - Zeta potential;
PSD - Particle size distribution

Effect of Glycerin Contents

Emulsions AS2, AS24 and AS25 differ in their glycerin content (2.25, 5, 7.5%, respectively). There was no significant change in the zeta potential in the mean droplet size between these emulsions. All the three emulsions were resistant to autoclave sterilization and to excessive shaking over 48 hours at 100 rpm.

Example 15

The emulsion AS2 and AS24 were gelified with 1–2% hydroethylcellulose Natrosol G, M™, and HHX™ (Hercules, The Hague, The Netherlands). The gel formulation was prepared by gentle stirring of the dispersed gel forming polymer with the emulsion for about 30 min. until the appropriate consistency was reached. As expected, the gels prepared with Natrosol G were less viscous than the gels prepared with Natrosol M and HHX.

Particle sized determination following appropriate dilution with an aqueous glycerin solution (2.25%) revealed no change. The gels were visually homogeneous and cosmetically acceptable.

Example 16

Various formulations were administered to eyes of 4 rabbits and the residence time of the preparations in the eye was determined by the use of fluorescent probes present in the preparations. The tested preparations consisted of two emulsions in accordance with the present invention, i.e. positively-charged emulsions, two negatively-charged emulsions and two aqueous preparations. The listed preparations were the following:

(i) Two positively-charged emulsions (AS2 from Example 14) with either 1% Rose Bengal or with 0.1% of a fluorometric probe (4-hepta-decyl-7-hydroxy-coumarin).

(ii) Negatively-charged emulsions with either 1% Rose Bengal or with 0.1% of the above fluorometric probe. The other ingredients of the emulsions were the following (% w/w):
MCT oil 4.0
Lipoid E-80⁻ 0.175
α-tocopherol 0.02
Miranol MHT™ solution (Venture Chemical Products Ltd., Reading, UK) 1.5
glycerin 2.25
distilled water to 100%

(iii) Aqueous solutions being either fluorescein eyedrops containing also a local anesthetic or a preservative and a solution of 1% Rose Bengal in sterile water.

The 4 rabbits were given 2 drops of one of the above preparations in each of their eyes and the eyes were then examined by a slit lamp (red-free light for the Rose Bengal formulations, polarized light for the fluorescein drops and regular light for the fluorimetric probe) over a period of 50 mins. The formulations administered to each of the rabbits (numbered arbitrarily as #1–#4) were the following: (RE—right eye; LE—left eye).

Rabbit #1—RE—(+) emulsion with fluorimetric probe
—LE—(−) emulsion with fluorimetric probe
Rabbit #2—RE—Rose Bengal in water
—LE—Rose Bengal in (+) emulsion
Rabbit #3—RE—Rose Bengal in water
—LE—Rose Bengal in (−) emulsion
Rabbit #4—RE—Fluorescein drops
—LE—Rose Bengal in (+) emulsion The following preliminary results were obtained:

Rabbit #1: RE—The fluorescein probe was clearly seen after 30 mins. and to some extent also after 38 mins.

LE—The preparation was instilled twice to the eye because it disappeared within 10 mins and the eye had been closed for over 4 mins. To rule out any effect from this closing, the preparation was instilled to the eye again. On the second time the fluorescein probe was almost totally gone after 21 mins. and disappeared completed after 27 mins.

Rabbit #2: RE—Rose Bengal was evident after 30 mins.

LE—Almost no Rose Bengal was evident after 25 mins, and none was evident after 30 mins. To rule out over-zealous wiping, 2 more drops of the preparation were instilled and after 18 mins only very little fluoresceins was evident and none was evident after 22 mins.

Rabbit #3: RE—The fluorescein signal began to fade after 28 mins and after 37 mins it was only evident on a cotton wool twist and not seen on the eye.

LE—Fluoresceins was still evident in the eye after 39 mins. In general, the dye was more evident in the LE, but both eyes showed fading fluoresceins with time. Twists of cotton wool applied to the conjuctiva were used to absorb the tear film there, and any dye present in them. In the case of Rose Bengal, cotton wool twists proved to be more sensitive than the slit lamp.

Rabbit #4: RE—Fluorescein was evident at 33 mins. At 40 mins none was seen on the eye after blinking, but some appeared apparently from the eyelashes.

LE—Eye was full of a pussy-looking discharge. Rose Bengal was still seen after 26 mins.

The above results show that generally, the positive emulsions remained on the eye longer than the negative emulsions. Regarding the Rose Bengal, which is presumably dissolved in the aqueous phase, it remained in the eye longer in the negative emulsions than in the water formulation whereas in the case of the latter it remained longer than in the case of the positive emulsion.

We claim:

1. A pharmaceutical or cosmetic composition comprising:
a pharmaceutically or cosmetically active effective amount of a hydrophobic active ingredient and a carrier, the carrier being an oil-in-water type emulsion which comprises colloid particles having an oily core surrounded by an interfacial film, said active ingredient being incorporated into said oily core, wherein said interfacial film comprises a cationic lipid, nonionic surfactant and an anionic surfactant or anionic lipid, said cationic lipid is in a concentration of 0.05–2% by weight and being selected from the group consisting of a $C_{10}$–$C_{24}$ primary alkylamine, a $C_{10}$–$C_{24}$ primary alkanolamine and a cholesterol ester, said nonionic surfactant is in a concentration of 0.05–3% by weight and being selected from the group consisting of poloxamers, tyloxapol, polysorbate, and polyoxyethylene fatty acid esters, said anionic surfactant or anionic lipid are phospholipids in a concentration of 0.5–3% by weight, wherein said colloidal particles have a positive zeta potential and an average particle size of about 0.1 to 1 micron.

2. A composition according to claim 1, wherein said cationic lipid are stearylamine or oleylamine.

3. A composition according to claim 1, wherein the concentration of said cationic lipid is about 0.1–0.4% (w/w).

4. A composition according to claim 1, wherein the phospholipid concentration is about 0.75–2% (w/w).

5. A composition according to claim 1, wherein the concentration of the oily core is about 3–20% (w/w).

6. A composition according to claim 5, wherein the concentration of the oily core is about 6–10% (w/w).

7. A composition according to claim 1, being a cosmetic composition and comprising a gel forming polymer.

8. A composition according to claim 1 wherein said cholesterol ester is cholesterol betainate.

9. A composition according to claim 1 wherein the composition is a parenteral composition.

10. A method for administration of a hydrophobic pharmaceutically or cosmetically active ingredient to a subject, wherein said active ingredient is administered within a carrier being an oil-in-water type emulsion which comprises colloid particles having an oily core surrounded by an interfacial film, said active ingredient being incorporated in to said oily core, wherein said interfacial film comprises a cationic lipid, nonionic surfactant and an anionic surfactant or anionic lipid, said cationic lipid is in a concentration of 0.05–3% by weight and being selected from the group consisting of a $C_{10}$–$C_{24}$ primary alkylamine, a $C_{10}$–$C_{24}$ primary alkanolamine and a cholesterol ester, said nonionic surfactant is in a concentration of 0.05–2% by weight and being selected from the group consisting of poloxamers, tyloxapol, polysorbate, and polyoxyethylene fatty acid esters, said anionic surfactant or anionic lipid are phospholipids in a concentration of 0.5–3% by weight, wherein said colloidal particles have a positive zeta potential and an average particle size of about 0.1 to 1 micron.

11. A method according to claim 10, wherein said cationic lipids are stearylamine or oleyamine.

12. A method according to claim 10, wherein the concentration of said cationic lipid is about 0.1–0.4% (w/w).

13. A method according to claim 10, wherein the phospholipid concentration is about 0.75–2% (w/w).

14. A method according to claim 10, wherein the concentration of the oily core is about 3–20% (w/w).

15. A method according to claim 14, wherein the concentration of the oily core is about 6–10% (w/w).

16. A method according to claim 10, wherein the administration is parenteral.

17. A method according to claim 10, wherein the administration is topical.

18. The method according to claim 10 wherein said cholesterol ester is cholesterol betainate.

* * * * *